(12) United States Patent
Arazawa et al.

(10) Patent No.: US 11,471,302 B2
(45) Date of Patent: *Oct. 18, 2022

(54) BONE GRAFT DELIVERY REVOLVER

(71) Applicant: Stryker European Operations Holdings LLC, Kalamazoo, MI (US)

(72) Inventors: David Arazawa, Hummelstown, PA (US); Brian Sechrist, Phoenixville, PA (US); Oliver Buchert, Franklin Lakes, NJ (US); Amir Ali Sharifi-Mehr, Bloomingdale, NJ (US)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/100,184

(22) Filed: Nov. 20, 2020

(65) Prior Publication Data
US 2021/0068978 A1 Mar. 11, 2021

Related U.S. Application Data

(62) Division of application No. 16/212,136, filed on Dec. 6, 2018, now Pat. No. 10,869,770.

(Continued)

(51) Int. Cl.
*A61B 17/88* (2006.01)
*A61F 2/46* (2006.01)

(52) U.S. Cl.
CPC ........ *A61F 2/4601* (2013.01); *A61B 17/8802* (2013.01); *A61B 17/8805* (2013.01); *A61B 17/8833* (2013.01); *A61F 2/4644* (2013.01)

(58) Field of Classification Search
CPC .. A61F 2/4601; A61F 2/4644; A61B 17/8802; A61B 17/8805; A61B 17/8833; F41A 9/85
See application file for complete search history.

(56) References Cited

U.S. PATENT DOCUMENTS 1,228,505 A * 6/1917 Wesson ............... F41A 9/85
42/89
3,377,732 A * 4/1968 Bivens ............... F41A 9/85
42/50

(Continued)

FOREIGN PATENT DOCUMENTS

EP 2774583 A1 * 9/2014 ......... A61B 17/8825

*Primary Examiner* — Zade Coley
(74) *Attorney, Agent, or Firm* — Lerner, David, Littenberg, Krumholz & Mentlik, LLP

(57) ABSTRACT

A device for loading bone graft material into a delivery tube is provided herein. The device includes a housing defining a reservoir for receiving bone graft, a magazine at least partially disposed within the housing, and an actuation member coupled to the housing for discharging the bone graft material into the delivery tube. The magazine defines a first chamber and a second chamber and is moveable between a first position in which the first chamber is in communication with the reservoir and a second position in which the second chamber is in communication with the reservoir. The actuation member includes a plunger configured to slide into the first chamber and the second chamber to discharge bone graft material, when bone graft material is contained therein, into the delivery tube. Methods of loading bone graft material are also provided.

20 Claims, 10 Drawing Sheets

Related U.S. Application Data

(60) Provisional application No. 62/597,143, filed on Dec. 11, 2017.

(56) References Cited

U.S. PATENT DOCUMENTS

| | | | |
|---|---|---|---|
| 3,520,299 | A | 7/1970 | Lott et al. |
| 4,531,938 | A | 7/1985 | Kaye et al. |
| 4,762,515 | A | 8/1988 | Grimm |
| 7,018,382 | B2 * | 3/2006 | Merboth ............... A61F 2/4644 606/93 |
| 8,118,813 | B2 | 2/2012 | Perez-Cruet et al. |
| 9,545,282 | B2 | 1/2017 | Mathur et al. |
| 9,668,881 | B1 | 6/2017 | Greenhalgh et al. |
| 2005/0101963 | A1 * | 5/2005 | Merboth ........... B05C 17/00553 606/92 |
| 2006/0079905 | A1 * | 4/2006 | Beyar ................ A61B 17/8816 606/76 |
| 2010/0010495 | A1 | 1/2010 | Foster |
| 2010/0256554 | A1 | 10/2010 | Discher, Jr. et al. |
| 2014/0257232 | A1 * | 9/2014 | Mathur ................ A61F 2/4601 604/500 |
| 2015/0040748 | A1 * | 2/2015 | Macy ....................... F41A 9/73 89/33.02 |
| 2015/0112352 | A1 | 4/2015 | Krause et al. |

\* cited by examiner

BONE GRAFT DELIVERY REVOLVER

CROSS-REFERENCE TO RELATED APPLICATIONS

This application is a divisional of U.S. patent application Ser. No. 16/212,136, filed on Dec. 6, 2018, which claims the benefit of the filing date of U.S. Provisional Patent Application No. 62/597,143, filed Dec. 11, 2017, the disclosures of which are each hereby incorporated herein by reference.

BACKGROUND OF THE INVENTION

The present invention relates to a device and methods for facilitating delivery of materials to bone during a surgical procedure, and more particularly, for loading bone graft or bone graft substitute material into an injector for percutaneous surgical procedures.

Various surgical procedures include the delivery of bone graft or bone graft substitute to promote bone growth between two bones or portions of bones. For instance, bone graft is typically used in spinal fixation procedures to aid in fixing and/or fusing vertebral bodies of the spinal column, whether alone or in combination with implants, screws, and/or the like. There is an increasing prevalence that these procedures be performed percutaneously in a minimally invasive way, which creates challenges.

In certain surgical procedures, facet joints of the spine may be fused, at least in part, by attaining access to the joints through a portal (such as a cannula) and placing or injecting bone graft into the joint area. For example, in one procedure, a surgeon places bone graft through a tube which is fixed to the operating room table via a flexible fixation arm. The graft is placed onto and around the joint little by little through the use of forceps repeatedly being placed into the surgical site.

This system generally involves several steps including loading a delivery tube multiple times with bone graft and continuously re-aligning the access portal in order to achieve sufficient placement of the bone graft. Furthermore, two hands are often required to reload and operate the system. This results in a cumbersome delivery procedure.

To simplify the delivery process, percutaneous bone graft delivery systems for injecting bone graft through a delivery tube to a delivery site have been developed, and are disclosed, for example, in U.S. Pat. Pub. No. 2015/0112352 ("the '352 Application"), assigned to applicant and incorporated by reference in its entirety herein as if set forth fully herein. Nevertheless, it would be desirable to provide a bone graft loading device that efficiently loads bone graft material into a delivery tube adapted to be used with a percutaneous bone graft delivery injector such as the device disclosed in the '352 Application.

BRIEF SUMMARY OF THE INVENTION

In accordance with a first aspect of the present invention, a device for loading bone graft material into a delivery tube is provided. The delivery tube may be configured to be removably securable to the device such that bone graft material may be loaded into the delivery tube and then subsequently attached to a separate bone graft injector device. Alternatively, the device may operate as a stand-along bone graft injector.

The device efficiently packs bone graft material into a plurality of chambers and then discharges each of the plurality of chambers into the delivery tube upon actuation of an actuation member. In one aspect of the invention, actuation of the actuation member both loads at least one of the plurality of bone graft chambers and discharges a different one of the chambers, thereby optimizing each actuation. Other preferred embodiments, as discussed hereinafter, ensure efficiency by allowing each of the plurality of chambers to sufficiently fill before discharging.

One embodiment of the device includes a housing defining a reservoir for receiving bone graft, a magazine at least partially disposed within the housing, and an actuation member coupled to the housing for discharging the bone graft material into the delivery tube. The magazine defines a first chamber and a second chamber and is moveable between a first position in which the first chamber is in communication with the reservoir and a second position in which the second chamber is in communication with the reservoir. The actuation member includes a plunger configured to slide into at least one of the first chamber and the second chamber to discharge bone graft material, when bone graft material is contained therein, into the delivery tube.

In a preferred embodiment, the actuation member is coupled to the housing and includes a plurality of y-shaped tracks for cooperating with a pin provided on the magazine. This configuration causes the magazine to rotate about its longitudinal axis, and relative to the housing from the first position to the second position, upon actuation of the actuation member. In one particular aspect, actuation of the actuation member rotates the magazine from the first position to the second position. The actuation member includes an ergonomically shaped push button for comfort and efficiency The magazine may include at least three chambers, each of which is brought into communication with the reservoir at least once during a revolution of the magazine to receive bone graft material contained within the reservoir. In some instances, at least two chambers of the at least three chambers are brought into communication with the reservoir as the magazine is rotated from the first position to the second position. In this configuration, where the magazine includes "n" number of chambers the magazine is preferably configured to rotate such that the plunger discharges each of the chambers one time during "n" number of actuations to ensure that each chamber is completely discharged.

In one aspect, the device is configured to be a stand-alone bone-graft injector. In an alternative aspect, the delivery tube is removable from the housing and configured to be attached to a separate bone graft injector device after it has been loaded.

The housing may further include a chimney for funneling the bone graft material contained in the reservoir to a bottom of the reservoir, and/or a ratcheting gear.

In another embodiment, the device includes a housing defining a reservoir for receiving bone graft material therein and a magazine at least partially disposed within the housing. The magazine defines a first chamber and a second chamber and is rotatable about a longitudinal axis of the magazine and relative to the housing between a first position in which the first chamber is in communication with the reservoir and the second chamber is isolated from the reservoir, and a second position in which the second chamber is in communication with the reservoir and the first chamber is isolated from the reservoir. The device being configured to load bone graft material into the first chamber and the second chamber when each of the first chamber and the second chamber are in communication with the reservoir.

The device may further include an actuation member that causes the magazine to rotate from the first position to the second position upon actuation thereof. The actuation member includes a plunger that slides into at least one of the first chamber and the second chamber upon actuation of the actuation member for discharging bone graft material contained therein.

Also provided herein is a method for loading bone graft material into a delivery tube. The method includes loading bone graft material into a reservoir defined in a housing, rotating a magazine about a longitudinal axis of the magazine and relative to the housing, between a first position and a second position, and actuating an actuation member coupled to the housing. The magazine defines a first chamber and a second chamber such that the first chamber is in communication with the reservoir in the first position and the second chamber is in communication with the reservoir in the second position. The actuation member includes a plunger configured to slide into at least one of the first chamber and the second chamber for discharging bone graft material, when bone graft material is contained therein, into the delivery tube. In one aspect, actuation of the actuation member rotates the magazine from the first position to the second position.

The delivery tube may optionally be removed from the housing, after it has been loaded, and attached to a separate bone graft injector.

DETAILED DESCRIPTION

As used herein, "axial" means along or parallel to the longitudinal axis of the magazine of the bone graft delivery device and "radial" means in the perpendicular direction thereto. "Rotation" refers to rotation about the longitudinal axis, unless otherwise described. "Interior" means radially inward, either toward or facing the longitudinal axis, and "exterior" means radially outward, or away from the longitudinal axis. The terms "proximal" and "distal", respectively, mean the end of the device nearest the surgeon or other user operating the device and the opposite end of the device furthest from the user operating the device.

Figure 1:
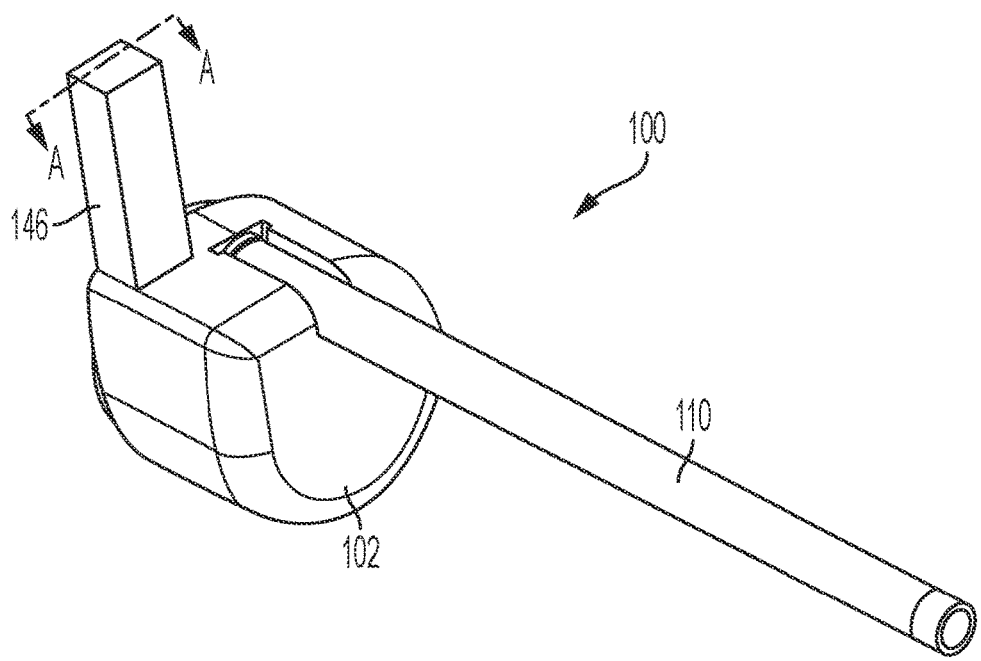
FIG. 1 is a perspective view of a bone graft delivery device according to an embodiment of the invention.
Figure 2:
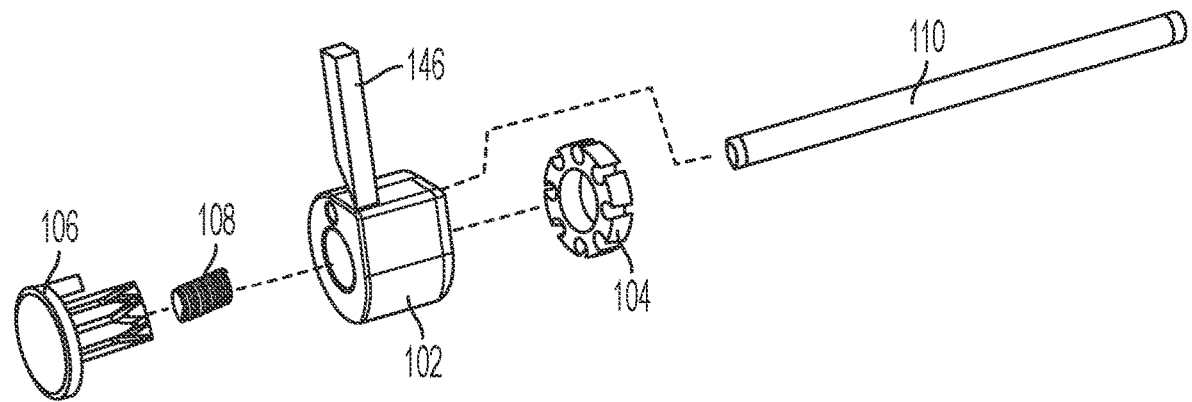
FIG. 2 is exploded view of the bone graft device of FIG. 1.

FIGS. 1 and 2 illustrate a device 100 for optimizing the loading of bone graft material into a delivery tube configured to be attached to a bone graft injector device. The term "bone graft" refers generally to bone graft, bone graft alternative, bone graft substitute, bone marrow aspirate, or mixtures thereof, whether occurring naturally or artificially. In one embodiment, the device 100 includes a housing 102, a magazine 104, an actuation member 106, a biasing member 108, and a delivery tube 110.

Figures 4A, 4B:
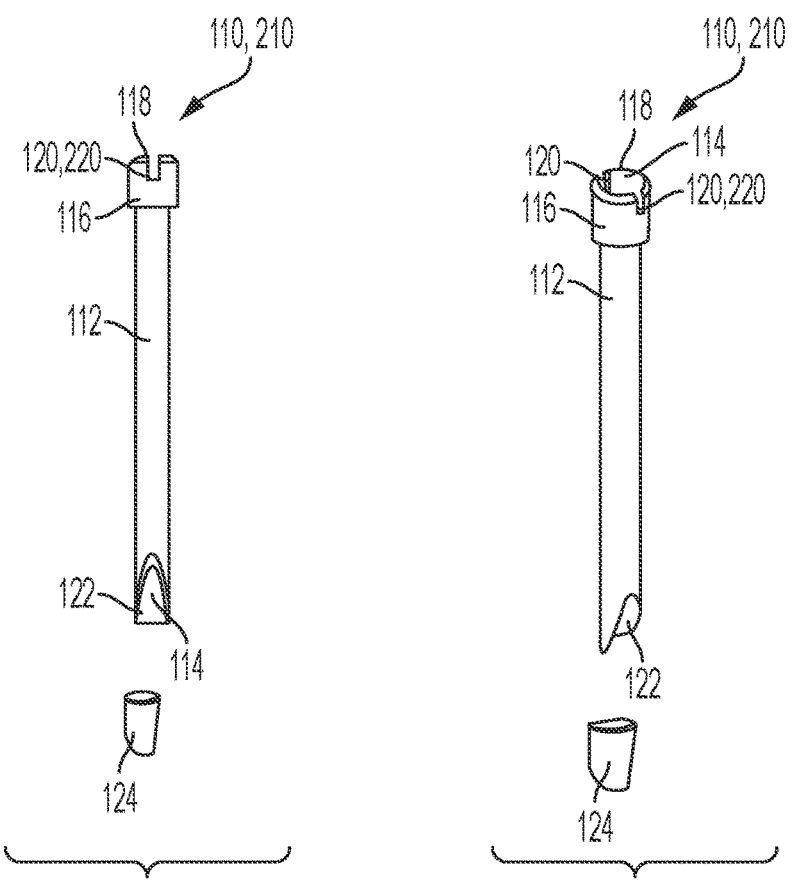
FIGS. 4A and 4B are front and topwardly facing perspective views, respectively, of a delivery tube of the bone graft delivery device of FIG. 1.

Delivery tube 110, or cannula, is illustrated in detail in FIGS. 4A and 4B. Cannula 110 generally includes a hollow cylindrical body 112, having a bore 114 extending therethrough, a base 116 provided at a proximal end 118 of body 112, optionally having a retaining mechanism 120 provided thereon, a delivery or distal end 122 opposite the proximal end 118, and a cap 124 adapted to close delivery end 122. Base 116 is cylindrical and has a larger diameter than body 112. One or more retaining mechanism 120 may optionally be provided on base 116 for removably securing cannula 110 to housing 102. As shown in FIGS. 4A and 4B, retaining mechanism 120 includes two diametrically opposed slots extending distally from a proximal end of base 116 configured to engage with diametrically opposed retaining tabs (not shown) provided on housing 102 for locking cannula 110 to housing 102. Alternatively, cannula 110 may be integrally formed with housing 102 or be secured to housing 102 using any suitable alternative securement mechanism, including for example, a friction fit, a cam lock, and/or threading.

Delivery or distal end 122 of body 112 may be an uninterrupted hollow cylinder, or, an interrupted hollow cylinder, as illustrated in FIGS. 4A and 4B. For example, delivery end 122 includes an off-axis exit portion having a generally "U" shaped portion cut out about a circumference of body 112. This configuration is useful in facilitating off-axis expulsion of the bone graft material through cannula 110. During loading of bone graft material and/or prior to use of device 100, cap 124 may be fit over distal end 122 for closing the same. Preferably, cannula body 112 is formed from a disposable biocompatible plastic that is preferably translucent or transparent, to allow a user to at least partially see bone graft material being loaded into and passing through cannula 110. Cannula body 112 preferably also includes indicia (not shown), such as laser markings, for indicating a volume of bone graft material disposed therein. Alternatively, cannula body 112 may be formed of a metal suitable for surgery.

Figure 5A:
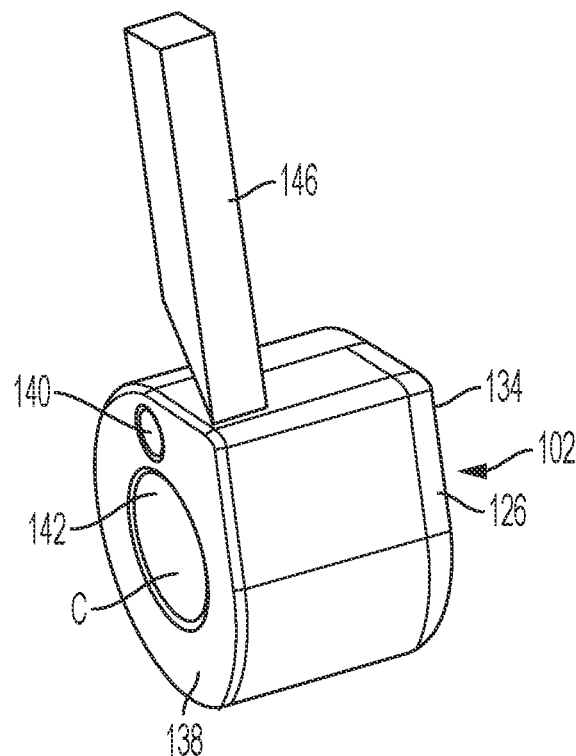
FIG. 5A is a perspective view of a housing including a packing member of the bone graft delivery device of FIG. 1.
Figure 5B:
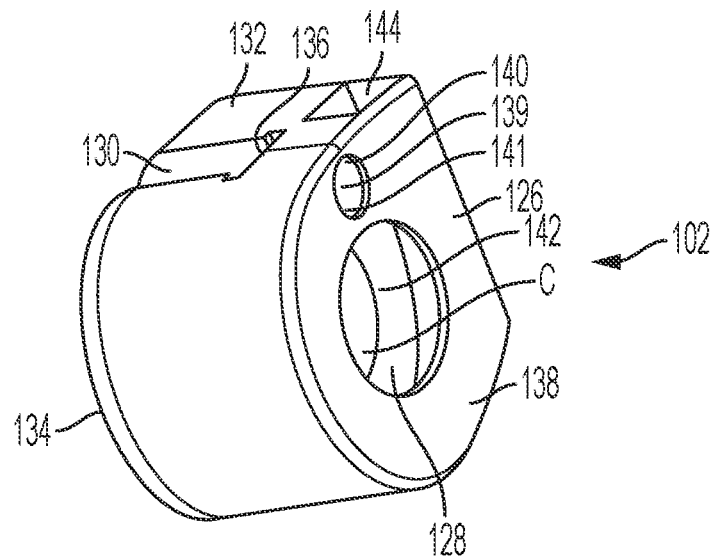
FIG. 5B is a rearwardly facing perspective view of the housing of FIG. 5A, without the packing member.

Housing 102, shown in detail in FIGS. 5A and 5B, may be any 3-dimensional shape having an outer surface 126 and an inner surface 128 defining an interior cavity C sized and shaped to receive at least a portion of magazine 104, actuation member 106, and biasing member 108. In aspects of the invention where cannula 110 is removeably connectable to housing 102 (e.g., not integrally formed therewith), a recess 130 is defined in a top surface 132 of housing 102 for receiving base 116 and optionally a proximal portion of cannula body 112 as shown in FIG. 1. Recess 130 extends from a distal end wall 134 of housing 102 to a recess end wall 136 provided at a location between distal end wall 134 of housing 102 and a proximal end wall 138 of housing 102. Corresponding retaining mechanisms (not shown) may be provided within recess 130 for cooperating with base 116 and/or retaining mechanism 120 for removeably securing cannula 110 to housing 102 as previously described.

Proximal end wall 138 of housing 102 defines a plunger aperture 140 and an actuation barrel aperture 142 spaced a distance apart from one another and configured to respectively receive portions of actuation member 106, as is described in further detail hereinafter. Actuation barrel aperture 142 extends through proximal end wall 138 and into cavity C of housing 102.

Plunger aperture 140 is axially aligned with recess 130 such that plunger aperture 140 extends continuously through outer surface 126 of proximal end wall 138 and through recess end wall 136 to form a loading channel 139 for loading the bone graft material into cannula 110. Loading channel 139 preferably has a diameter equal to or less than a diameter of bore 114, defined in cannula body 112, such that bone graft material is not squeezed through a condensed diameter during the loading process which may cause dehydration of the bone graft material.

Housing 102 also defines a reservoir 144 for receiving bone graft material therein. Reservoir 144 extends through top surface 132 and empty into cavity C of housing 102. The walls of reservoir 144 may be angled or slopped so as to funnel bone graft material toward the cavity C. In one embodiment, as illustrated by FIG. 5B, the reservoir 144 is positioned adjacent proximal end wall 138 and be axially offset from loading channel 139. A packing member 146, having a packing end including an arcuate cut-out, may be inserted into reservoir 144 for aiding gravity in pushing bone graft material into reservoir 144 and toward magazine 104 as shown in FIG. 3.

Figure 3:
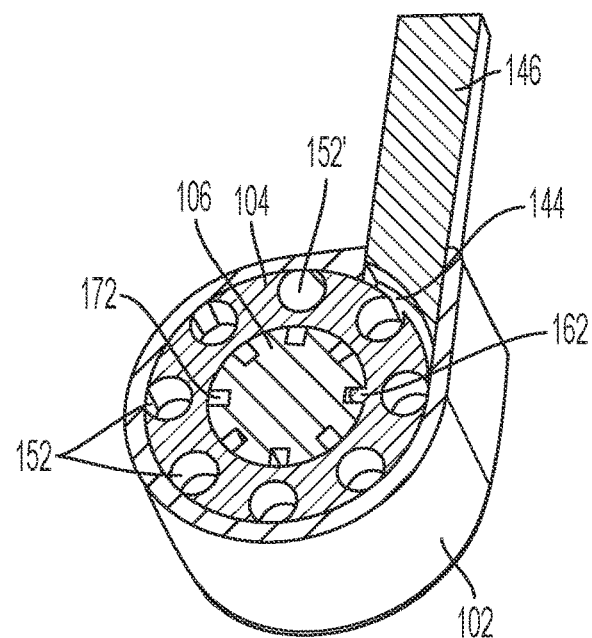
FIG. 3 is a rearwardly facing, cross-section view of the bone graft delivery device of FIG. 1 taken along line A-A.
Figure 6:
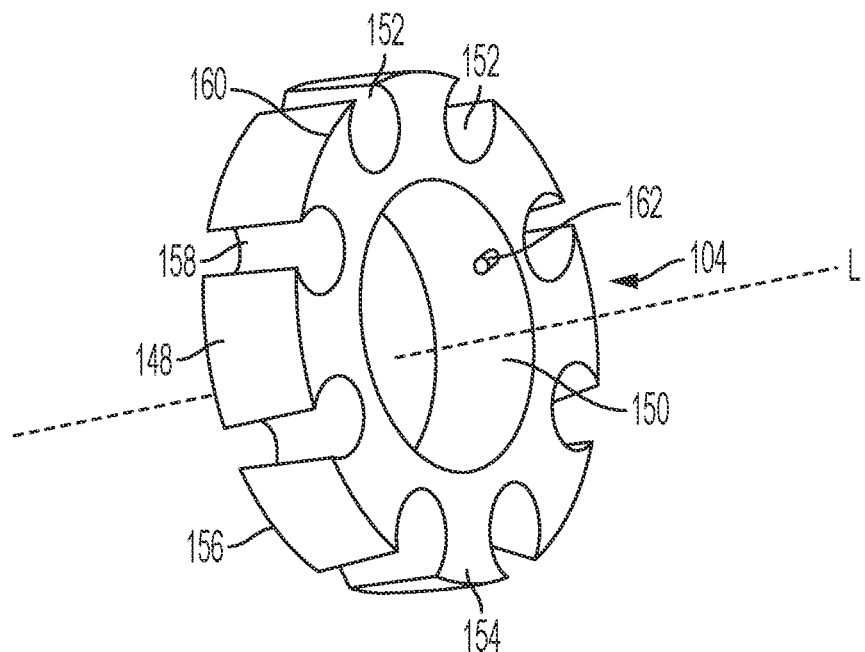
FIG. 6 is a perspective view of a magazine of the bone graft delivery device of FIG. 1.

As shown in FIGS. 3 and 6, magazine 104 is be generally wheel shaped, and thus, is referred to interchangeably hereinafter as bone graft wheel. Graft wheel 104 includes a longitudinal axis L, an outer circumferential wall 148, an inner circumferential wall 150, and a plurality of bone graft chambers 152, circumferentially provided about longitudinal axis L. Each of the bone graft chambers 152 extends completely through bone graft wheel 104 from a proximal end wall 154 to a distal end wall 156 thereof and is preferably provided adjacent an outer perimeter 160 of bone graft wheel 104 such that a channel 158 is formed through outer circumferential wall 148.

With specific reference to FIG. 3, graft wheel 104 is at least partially disposed within housing 102 such that movement of graft wheel 104 (e.g., rotational movement) will bring each of the chambers 152 into alignment with reservoir 144 allowing bone graft material to be transferred from reservoir 144, through channels 158, and into each of the plurality of chambers 152. As the bone graft wheel 104 rotates, each of the bone graft chambers 152 will be in communication with the reservoir 144 at least once during a single revolution of the bone graft wheel 104. During rotation, each of the chambers 252 will also be brought into proper loading alignment, meaning each of the chambers 252 will take turns being positioned within the loading channel 139 (the chamber positioned within loading channel 139 is hereinafter referenced by 152').

Figure 8A:
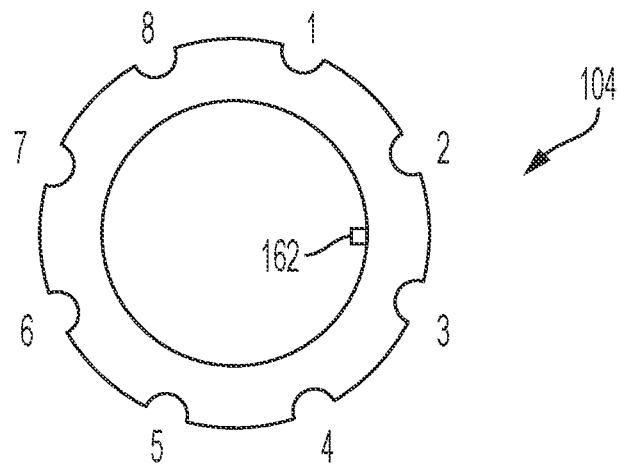
FIG. 8A is a schematic representation depicting sequential dischargment of the chambers of the magazine of FIG. 6.
Figure 8B:
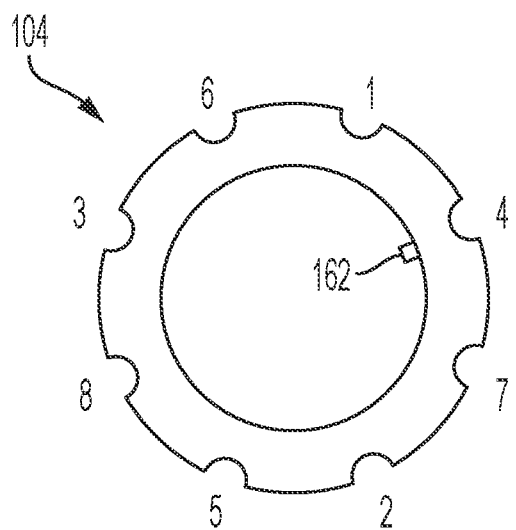
FIG. 8B is a schematic representation of an exemplary, non-sequential dischargment of the chambers of the magazine of FIG. 6.
Figure 8C:
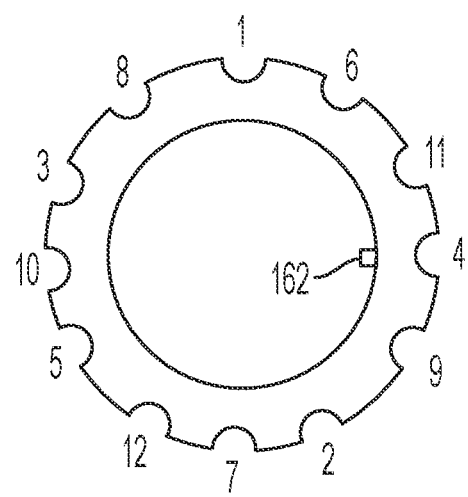
FIG. 8C is a schematic representation of an exemplary non-sequential dischargment of the chambers of an alternative magazine.

An inwardly extending pin 162 is provided on inner circumferential wall 150 of bone graft wheel 104 for cooperating with actuation member 106 to rotate graft wheel 104, as is further explained below. Although the magazine illustrated in FIGS. 2, 3, 6, 8A, and 8B depicts eight bone graft chambers, it is explicitly understood that that the bone graft wheel 104 may encompass any number of a plurality of chambers, for example, twelve chambers as shown in FIG. 8C.

Figure 7:
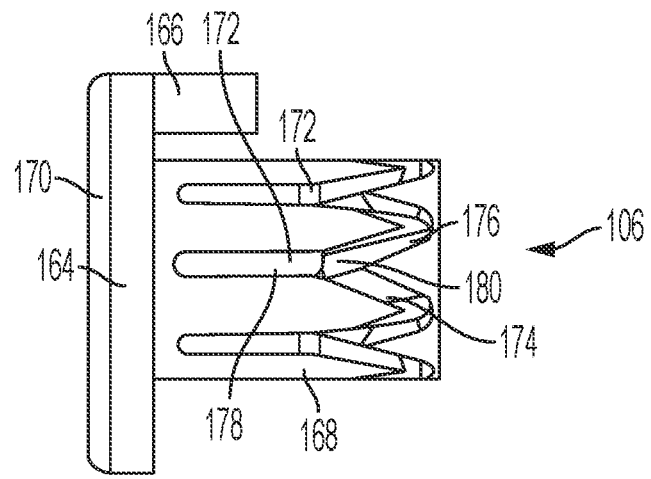
FIG. 7 is a side view of an actuation member of the bone graft delivery device of FIG. 1.

FIG. 7 illustrates an exemplary embodiment of actuation member 106. Actuation member 106 generally defines an actuation plate 164 having a plunger 166 and an actuation barrel 168 extending distally therefrom. The actuation plunger 166 and actuation barrel 168 are sized and shaped to extend through plunger aperture 140 (and into loading channel 139) and actuation barrel aperture 142, respectively. In a preferred embodiment, a rear surface of actuation plate 164 includes an ergonomically shaped push-button 170 such that a user can repeatedly and comfortably actuate actuation member 106 using only his or her thumb.

Actuation barrel 168 includes a plurality of y-shaped tracks 172 defined in an outer circumferential wall thereof. Each of the y-shaped tracks 172 is sized and shaped to receive pin 162 and includes a first portion 174, a second portion 176, and a stem portion 178, which intersect at intersection 180. As is illustrated in FIG. 7, stem portion 178 extends axially along the circumferential wall of actuation barrel 168, while first portion 174 and second portion 176 are angularly offset thereto.

Referring back to FIG. 2, biasing member 108, which may be a spring such as a helical spring, is provided between actuation member 106 and housing 102 coupling the same. Referring to FIGS. 2 and 7, when a user presses button 170, actuation plate 164 moves distally toward proximal end wall 138 of housing 102 and pin 162 rides from a distal end of first portion 174 of y-shaped track 172 toward intersection 180. The axial angle of first portion 174 causes the graft wheel 104 to rotate about its longitudinal axis L, for example, in a counter-clockwise direction until pin 162 reaches intersection 180. When pin 162 enters stem portion 178 of y-shaped track 172, graft wheel 104 dwells as the plunger 166 extends through the plunger barrel aperture 140 and the bone graft chamber 152' aligned therewith, thereby forcing bone graft material disposed in aligned bone graft chamber 152' through loading channel 139 and into bore 114 of cannula body 112.

After push-button 170 is released, actuation member 106 is biased away from housing 102 such that pin 162 rides from a proximal portion of stem 178 toward intersection 180. Due to the angle at which first portion 174 and second portion 176 branch from stem 178, pin 162 automatically enters second portion 176 of y-shaped track 172 when pin 162 travels in a proximal-distal direction. When pin 162 enters second portion 176, bone graft wheel 104 further rotates, for example, in the counter-clockwise direction. It is understood that by manipulating the number of y-shaped tracks and/or the angle at which first portion 174 and second portion 176 branch from stem 178, the direction and/or degree of rotation per-actuation of the actuation member 106 can be altered.

As graft wheel 104 rotates, each of the plurality of bone graft chambers 152 are brought into communication with reservoir 144 at least once during a single revolution of graft wheel 104.

In one embodiment of the present invention, each of the plurality of bone graft chambers 152 is filled and discharged in sequential order. For example, each of the plurality of the chambers 152 are filled as they are brought into communication with reservoir 144 and subsequently discharged as bone graft wheel 104 is rotated one position at a time, as is shown in FIG. 8A, schematically depicting the order in which the chambers are discharged.

Alternatively, in a preferred embodiment, bone graft wheel 104 may be rotated a plurality of chambers per actuation such that at least one of the bone graft chambers 152 is skipped over (i.e. not discharged by plunger 166) per actuation of actuation member 106. In this configuration, each of bone graft chambers 152 experience multiple revolutions before being discharged. Since each of the chamber 152 are brought into communication with reservoir 144 a plurality of times prior to having bone graft material discharged therefrom, the chambers 152 each have multiple chances to collect bone graft material, thereby increasing the likelihood that each of the chambers 152 will be sufficiently filled with bone graft material before being discharged. In this embodiment, it is preferred that the number of y-tracks provided is not a multiple of the number of bone graft chambers so as to ensure that all of the chambers will eventually be discharged. As is schematically represented by FIGS. 8B and 8C, in a preferred embodiment, device 100 can be optimized by choosing a number of y-tracks "n-y" relative to a number of bone graft chambers "n-c", such that each of the chambers 152 will be discharged once per a number of actuations "n-a", where the number of actuations "n-a" is equal to the number of chambers "n-c".

To use device 100, a user, such as a surgeon, first secures cannula 110 to housing 102 (if cannula 110 is not integrally formed therewith), as described above, and loads bone graft material into reservoir 144 defined in housing 102. Optionally, using packing member 146, the user may lightly pack the bone graft material, so as to avoid dehydrating it, toward a bottom of reservoir 144 and outer circumferential wall 148 of bone graft wheel 104.

Using his or her thumb, a user then presses push-button 170, causing actuation member 106 to move distally with respect to housing 102 and pin 162 to cooperate with y-shaped track 172. As previously detailed, as pin 162 slides along y-shaped track 172, bone graft wheel 104 is forced to rotate about its longitudinal axis L. Rotation of bone graft wheel 104 brings each of the plurality of chambers 152 into communication with reservoir 144, at least once per rotation, such that bone graft material is transferred from reservoir 144 to each of the bone graft chambers 152. Moreover, each actuation or compression of actuation member 106 also forces plunger 166 to slide through plunger aperture 140, and bone graft chamber 152' aligned therewith, forcing bone graft material contained therein into bore 114 of cannula body 112. The user may rapidly and continually actuate the device 100 until cannula 110 has been fully packed. After cannula 110 has been packed, it may be detached from housing 102 and secured to another bone graft injector for use during a percutaneous surgical procedure. Alternatively, after cap 124 is removed the device 100 may be continually actuated to discharge bone graft material from delivery end 122 of cannula 110.

The above described device 100 efficiently packs bone graft material into cannula 110 as each actuation member loads at least one of the plurality of bone graft chambers 152 and discharges a different one of the chambers 152, thereby optimizing each actuation. Moreover, the preferred embodiment, illustrated by FIGS. 8B and 8C, further ensures efficiency by allowing each of the plurality of chambers 152 to sufficiently fill before it is discharged.

Figure 9:
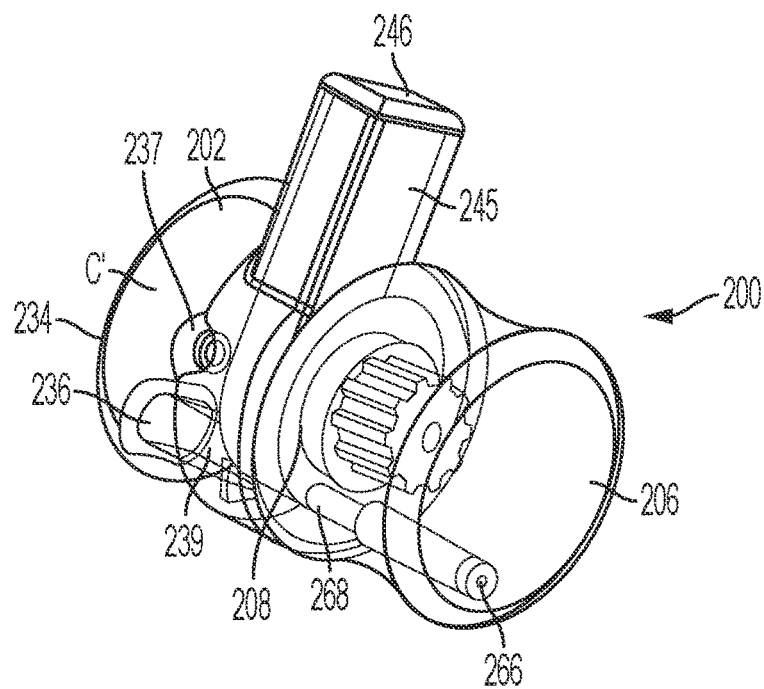
FIG. 9 is a perspective view of a bone graft delivery device according to another embodiment of the invention.
Figure 10:
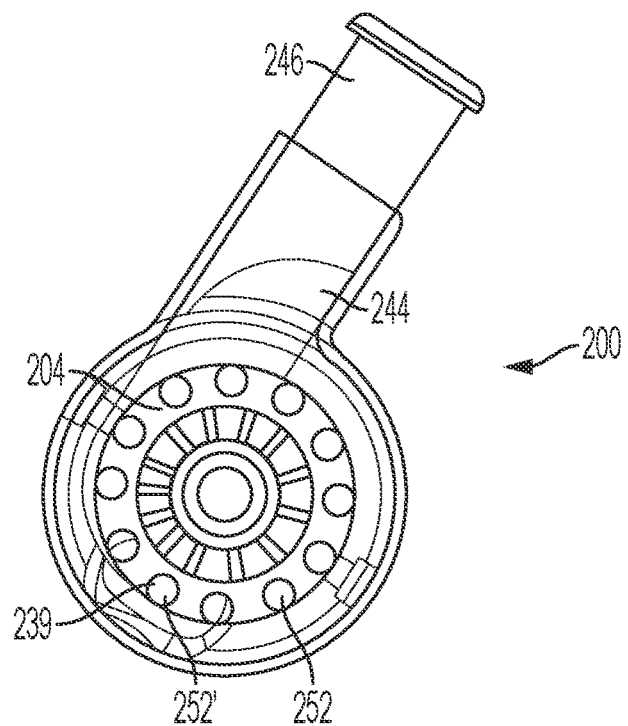
FIG. 10 is a front view of the bone graft delivery device of FIG. 9.

FIGS. 9 and 10 illustrate another embodiment of the invention for optimizing loading of bone graft material into a tube. In this embodiment, device 200 is configured to efficiently load delivery tubes sized and configured to be attached to other bone graft injector devices. The device 200 generally includes a housing 202, a magazine 204, a lid 206, a ratcheting gear 208, and a delivery tube 210.

The delivery tube 210, or cannula, is substantially similar to cannula 110, shown in FIGS. 4A and 4B, except as described hereinafter. Cannula 210 includes a retaining mechanism 220, which may be a helical thread or a cam-lock, such that cannula 210 is removably secured to housing 202 via a twisting force. However, it is understood that other known retaining mechanisms, such as interlocking tabs and or a friction fit, may additionally and/or alternatively be used.

Figure 11:
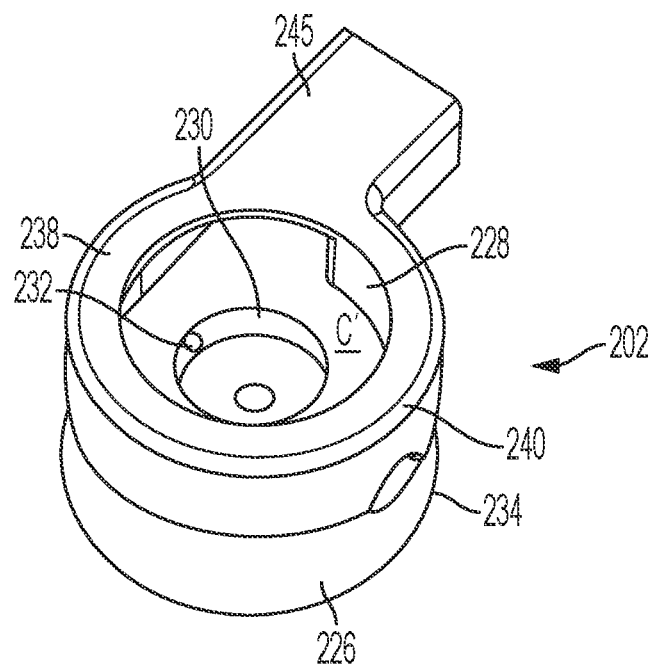
FIG. 11 is a perspective view of a housing of the bone graft delivery device of FIG. 9.

FIGS. 9-11 illustrate housing 202 in detail. Housing 202 may be any 3-dimensional shape having an outer surface 226 and an inner surface 228 defining an interior cavity C' sized and shaped to receive magazine 204, ratcheting gear 208, and at least a portion of lid 206, for retaining magazine 204 and ratcheting gear 208 therein. Cavity C' includes a circular track 230 configured to receive a portion of magazine 204. The circular track 230 has at least one locking member 232 provided thereon. The locking member 232 includes a hemispherical portion extending inwardly from track 230 for interacting with magazine 204 as is described in detail hereinafter. The at least one locking member or hemispherical member 232 may be formed of silicon, rubber, or other resiliently compressible material. Alternatively, the hemispherical member 232 may be moveably secured to track 230 such that locking members 232 moves radially toward and radially away from track 230.

A distal wall 234 of housing 202 defines an aperture 236 about which a retaining mechanism having a corresponding feature to retaining mechanism 220 is provided for removably securing cannula 210 to housing 202. The aperture 236 extends from outer surface 226 into cavity C' and forms a loading channel 239 for loading the bone graft material into cannula 210 (FIGS. 4A and 4B). Proximal end 238 of housing 202 may be substantially open and include an edge 240 for securing lid 206, for example, via a friction fit. Distal wall 237 also defines an aperture 237 through which a hex key (not shown), for example, may be inserted to rotate magazine 204 as is described in further detail hereinafter.

Housing 202 also defines a reservoir 244 for receiving bone graft material therein. In one particular embodiment, the reservoir 244 is defined by a chimney 245 extending through a top surface of housing 202 and emptying into cavity C', and more particularly, adjacent track 230. With specific reference to FIG. 10, a packing member 246, which includes a packing end having an arcuate cut-out, may be inserted into reservoir 244 for lightly packing bone graft material toward a bottom of reservoir 244 and toward magazine 204.

Figure 12:
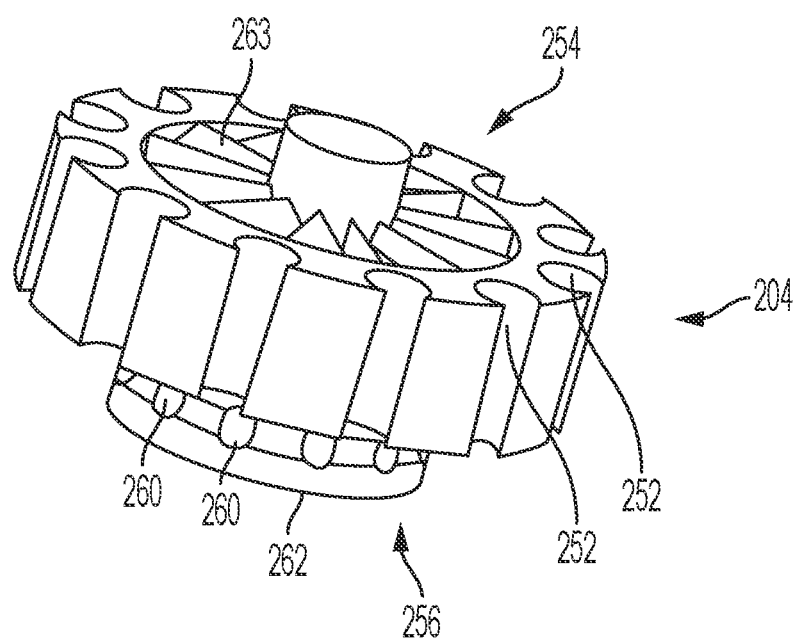
FIG. 12 is a perspective view of a magazine of the bone graft delivery device of FIG. 9.

As is shown in FIG. 12, magazine 204, also referred to as bone graft wheel, is substantially similar to bone graft wheel 104, but for the differences discussed below. For example, bone graft wheel 204 includes barrel 262 provided on a distal end 256 thereof. Barrel 262 defines a plurality of ball-like detents 260 circumferentially defined in an outer surface of barrel 262 that preferably correspond in number and angular disposition to bone graft chambers 252. Accordingly, as is further described below, the device 200 may quickly be brought into proper loading alignment by rotating bone graft wheel 204 until hemispherical members 232 are received by detents 260 temporarily locking bone graft wheel 204 in place. As used herein, proper loading alignment means at least one of the bone graft chambers 252 is positioned within the loading channel 239 (chamber aligned within loading channel 239 being referenced by 252'). After the aligned chamber 252' has been discharged, a rotational force may again be applied to bone graft wheel 204 causing the hemispherical member 232 to temporarily compress and allowing the bone graft wheel 204 to rotate to its next position, where hemispherical member 232 is received in an adjacent detent 260 and an adjacent bone graft chamber 252, in the direction of rotation, is positioned within loading channel 239.

Figure 13:
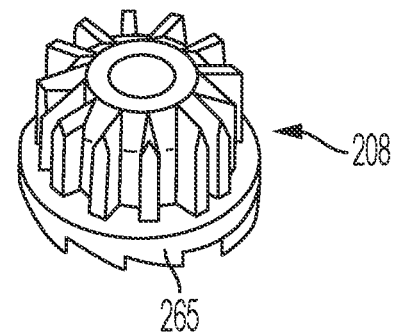
FIG. 13 is a perspective view of a ratcheting gear of the bone graft delivery device of FIG. 9.

Proximal end 254 of bone graft wheel 204 includes a plurality of angled slats 263 for coacting with ratcheting gear 208 (shown in FIG. 13), and more particularly, with corresponding slats 265 provided at a distal end of ratcheting gear 208, to ensure that bone graft wheel 204 only rotates in a single direction, for example, counter-clockwise.

As is shown in FIG. 9, a lid 206 closing open proximal end 238 of housing 202 may be snapped or friction fit thereto. Lid 206 is preferably transparent, to allow a user to visualize the inner components of device 200 including rotation of bone graft wheel 204.

In one embodiment, lid 206 is integrated with an actuation member 266, which may be, for example, a spring loaded plunger. Alternatively, lid 206 defines an aperture through which actuation member 266 extends. Lid 206 is shaped to engage edge 240 such that a distal or discharging end 268 of actuation member 266 is automatically, axially aligned with loading channel 239 and is positioned adjacent discharging or aligned bone graft chamber 252'.

To use device 200, a user, such as a surgeon, snaps or friction fits lid 206 to housing 202, inserts cannula 210 within aperture 236, and loads bone graft material into reservoir 244, as described above. Optionally, using packing member 246, the user may lightly pack the bone graft material, so as to avoid dehydrating it, toward a bottom of reservoir 244 adjacent bone graft wheel 204.

The user then rotates bone graft wheel 204, using a hex key or other device, from a first position to a second position, which preferably may be at least one full revolution to bring the reservoir 244 into communication with each of the bone graft chambers 252 and to load bone graft material therein. Alternatively, bone graft wheel 204 may be rotated from a first position to a second position, where the second position is less than one full revolution from the first position. After a sufficient amount of bone graft material has been loaded into each of the chambers 252, a user depresses the spring loaded plunger 266, causing a discharging end 268 thereof to slide through discharging channel 252' and force bone graft material contained therein into bore 214 of cannula body 212. After the bone graft material has been discharged, the user releases the actuation member 266 and discharging end 268 of the spring loaded plunger is biased in a proximal direction out of discharging chamber 252'. The surgeon may then quickly discharge another chamber by rotating bone graft wheel 204 until hemispherical member 232 is received by an adjacent detent 260 temporarily locking bone graft wheel 204 in a new discharging position such that an adjacent bone graft chamber 252 is aligned within the loading channel 239 for discharging. This procedure may be repeated until all of the chambers have been discharged or the cannula 210 has been fully packed. After cannula 210 has been packed, it may be detached from housing 202 and secured to another bone graft injector for use during a percutaneous surgical procedure.

Figure 14:
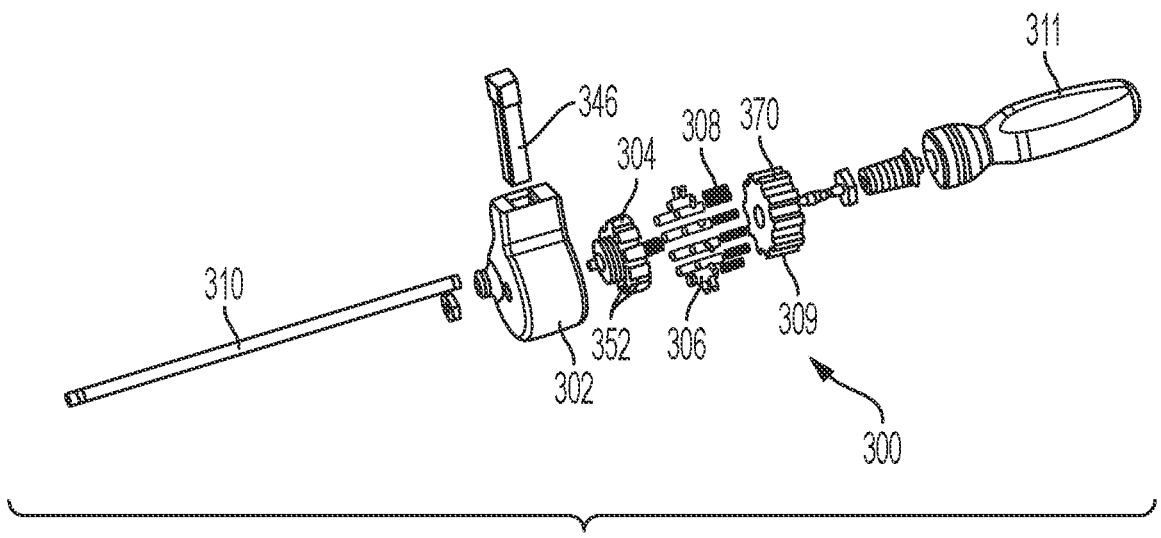
FIG. 14 is a perspective exploded view of a bone graft delivery device according to another embodiment of the invention.
Figure 15A:
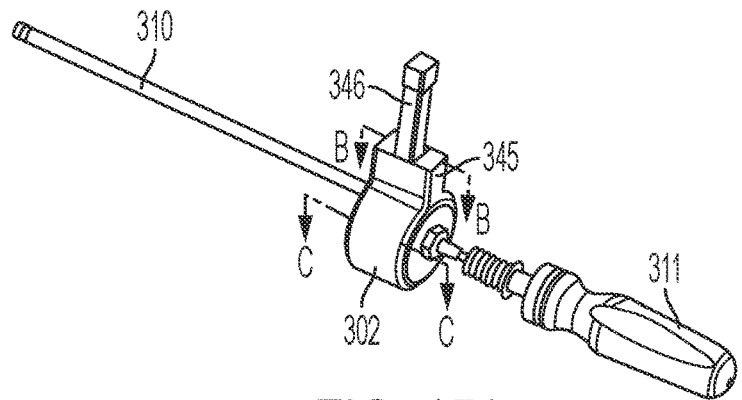
FIG. 15A is a perspective partially exploded view of the bone graft delivery device of FIG. 14.
Figure 15B:
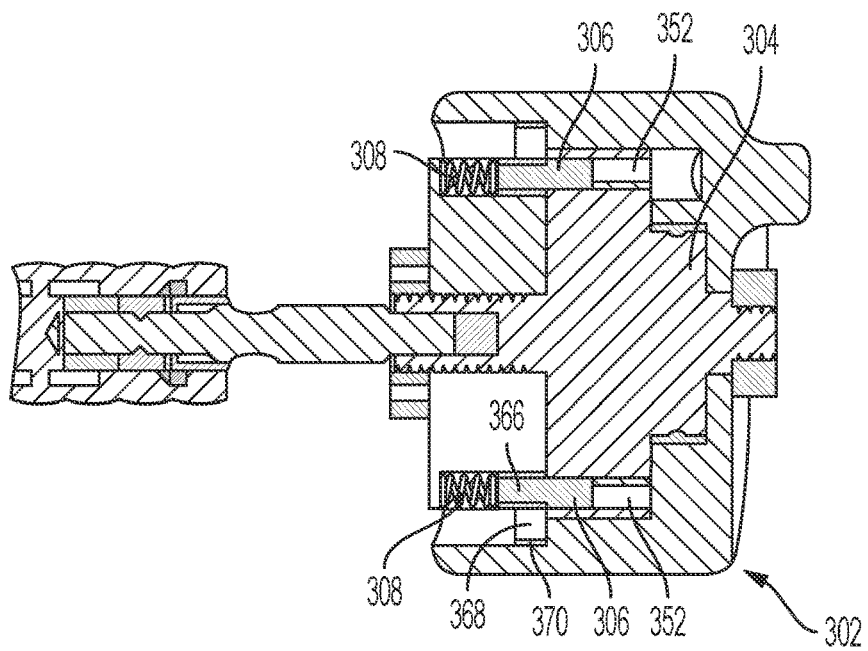
FIG. 15B is a cross section view of FIG. 15A taken along line B-B.
Figure 15C:
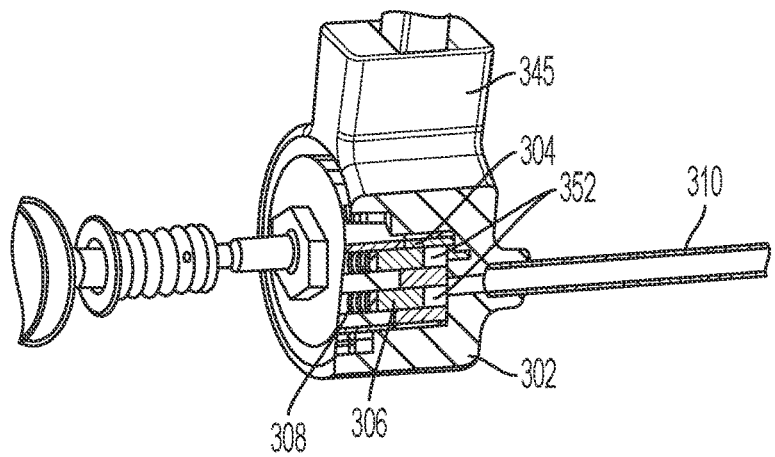
FIG. 15C is a cross section view of FIG. 15A taken along line C-C.

FIGS. 14-15C illustrate another embodiment of the invention for optimizing loading of bone graft material into a tube. In this embodiment, device 300 efficiently loads and discharges bone graft material into the tube using only a rotary movement. The device 300 includes a housing 302, a magazine 304, a plurality of actuation members 306, a plurality of biasing members 308, a cover 309, a delivery tube 310, and a handle 311.

Delivery tube 310, or cannula, is substantially similar to cannula 210 (FIGS. 4A and 4B) and may be removably securable to housing 302 as described above.

FIGS. 16A-16D illustrate housing 302, which may be any 3-dimensional shape having art outer surface 326 and an inner surface 328 defining an interior cavity C'' sized and shaped to receive magazine 304, plurality of actuation members 306, plurality of biasing members 308, and at least a portion of cover 309. A distal wall 334 of housing 302 defines an aperture 336 through which cannula 310 may be inserted and secured as previously described. The aperture 336 extends from outer surface 326 into cavity C'' and forms a loading channel 339 for loading the bone graft material into cannula 310. Proximal end 338 of housing 302 is substantially open for receiving and securing cover 309, for example, via a friction fit.

Cavity C'' includes a track 330 configured to receive magazine 304 and allow rotation of magazine 304 therearound. A ledge 340 encircles track 330 and includes a first portion 341, a second portion 342, and an intermediate portion 343 positioned between first portion 341 and second portion 342. Intermediate portion 343 is angularly aligned with loading channel 341, with respect to a longitudinal axis of housing 302. First portion 341 is spaced a greater distance from distal wall 334 than second portion 342 such that bone graft is automatically discharged as actuation members 306 transition from first portion 341 to second portion 342, as is further explained hereinafter.

Housing 302 also defines a reservoir 344 for receiving bone graft material. In this embodiment, the reservoir 344 is defined by a chimney 345 extending through a top surface of housing 302 and emptying into cavity C'', and more particularly, adjacent track 330 at a location that is angularly spaced from intermediate portion 343. Packing member 346 is substantially similar to packing member 246 and may be used for packing bone graft material into reservoir 344. Magazine 304, or bone graft wheel, is substantially similar to bone graft wheel 204, but may additionally include a proximally facing threaded member 362 extending along a longitudinal axis thereof for threadably engaging with handle 311 to facilitate rotation of the magazine 304.

Figure 16A:
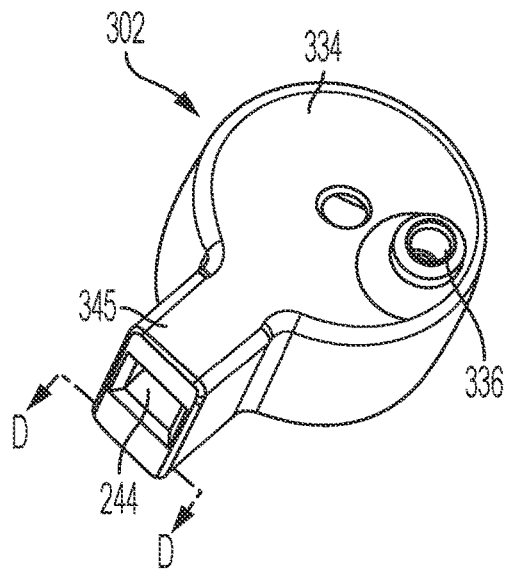
FIG. 16A is a distally facing perspective view of a housing of the bone graft delivery device of FIG. 14.
Figure 16B:
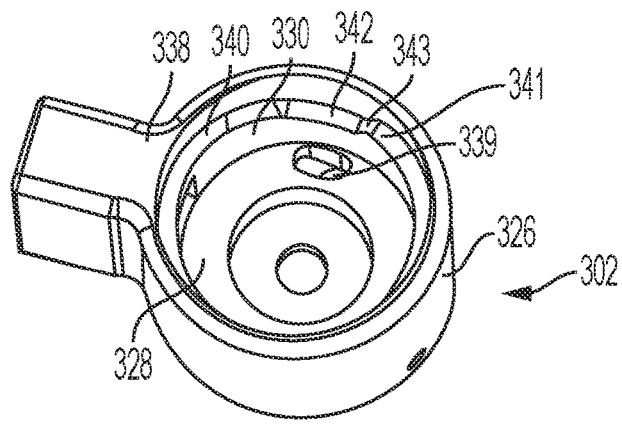
FIG. 16B is a proximally facing perspective cross-section view of the housing of FIG. 16A taken along line D-D.
Figure 16C:
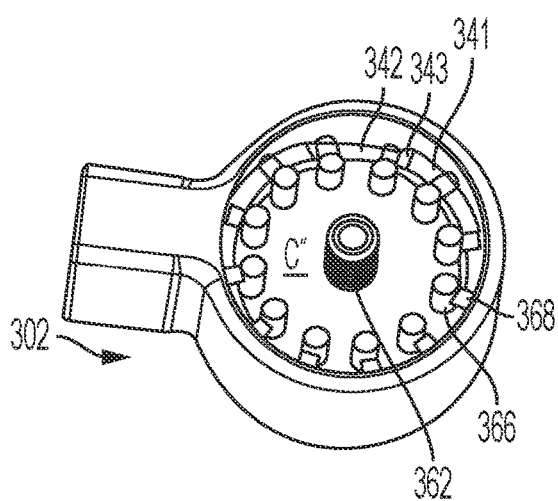
FIG. 16C is a proximally facing perspective cross-section view of the housing of FIG. 16A taken along line D-D with a magazine and actuation members contained within in the housing.
Figure 16D:
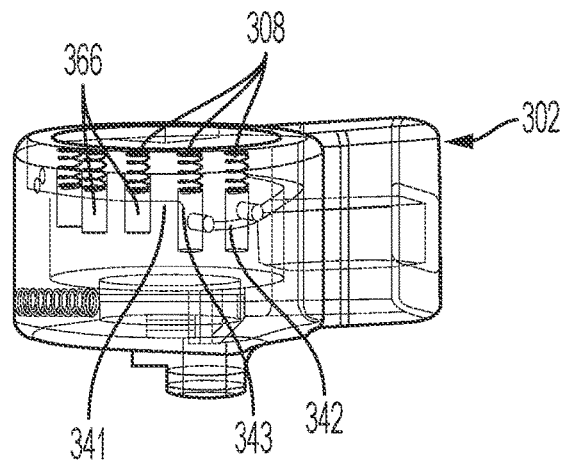
FIG. 16D is a wire framed perspective view of the housing of FIG. 16A.

Device 300 preferably includes an actuation member 306 and a biasing member 308, in the form of a helical spring, for each of the plurality of chambers 352. Each of the actuation members 306 being coupled to magazine 304 and configured to rotate therewith. When device 300 is assembled, as shown in FIG. 16D (magazine 304 removed for clarity), each of the helical springs 308 are provided between cover 309 and a corresponding actuation member 306. With reference to FIG. 16C, actuation members 306 include a plunger 366 for sliding into its corresponding chamber 352 and discharging bone graft material and a retaining portion 368, or cam-follower, for engaging with a slot 370 defined in cover 309 and cooperating with ledge 340. Prior to discharge, cam-follower 368 is positioned on first portion 341 of ledge 340 and its corresponding helical spring 308 is in a compressed state. As magazine 304 is rotated, cam-follower 368 is rotated about ledge 340. Upon reaching intermediate portion 343, cam-follower 368 shifts from first portion 341 to second portion 342, such that helical spring 308 expands and biases plunger 366 into its corresponding chamber 352 for discharging bone graft material from its corresponding discharging chamber into loading channel 239.

To use device 300, a user, loads bone graft material into reservoir 344. Optionally, the user may lightly pack the bone graft material, so as to avoid dehydrating it, toward a bottom of reservoir 344 adjacent bone graft wheel 304 using packing member 346. By twisting handle 311, the user rotates the magazine 304 from a first position to a second position and in the process brings one or more chambers 352 into communication with the reservoir 344, thereby loading bone graft material into each of these chambers 352.

As the user continues to rotate magazine 304, cam-follower 368 ride along first portion 341 of ledge 340 until plunger 366 transitions to second portion 342 at which point helical spring 308 expands and forces plunger 366 to slide into its corresponding discharging chamber and discharge the bone graft contained therein through loading channel 339 and into cannula 310.

The above described device 300 efficiently packs bone graft material into cannula 310 as a single rotary motion loads one chamber and simultaneously discharges a different chamber.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of loading a substance into a delivery tube comprising:
    moving a magazine defining a first chamber and a second chamber relative to a reservoir between a first position in which the first chamber is in communication with the reservoir and a second position in which the second chamber is in communication with the reservoir;
    dispensing the substance from the reservoir into the first chamber when the magazine is in the first position and dispensing the substance from the reservoir into the second chamber when the magazine is in the second position;
    actuating an actuation member to slide a plunger into at least one of the first chamber or the second chamber to discharge the substance into the delivery tube; and
    detaching the delivery tube from a housing at least partially surrounding the magazine.

2. The method of claim 1, further comprising attaching the delivery tube to an injector.

3. The method of claim 1, wherein the substance is a bone graft material.

4. The method of claim 1, wherein the moving step comprises rotating the magazine relative to the reservoir about a longitudinal axis of the magazine.

5. The method of claim 4, wherein the rotating step comprises rotating a handle coupled to the magazine to rotate the magazine about the longitudinal axis.

6. The method of claim 4, wherein the rotation of the magazine is guided by cooperation between a pin on the magazine and a plurality of y-shaped tracks.

7. The method of claim 1, wherein the actuating step comprises pressing a push button.

8. The method of claim 7, wherein the push button is pressed with a force that overcomes a biasing force supplied by a biasing member.

9. The method of claim 1, wherein the actuating step moves the magazine from the first position to the second position.

10. The method of claim 1, further comprising moving the magazine to a third position in which a third chamber of the magazine is in communication with the reservoir.

11. The method of claim 10, further comprising dispensing the substance from the reservoir into the third chamber when the magazine is in the third position.

12. The method of claim 11, wherein the actuating step rotates the magazine from the first position to the third position and wherein the second chamber and the third chamber are brought into communication with the reservoir as the magazine is rotated from the first position to the third position.

13. The method of claim 1, further comprising loading the substance into a reservoir.

14. The method of claim 13, wherein the loading step further comprises:
    loading the substance into a chimney and funneling the substance to a bottom of the reservoir; and
    packing the substance toward the bottom of the reservoir using a packing member.

15. A method of injecting a substance into a patient comprising:
    accessing a tissue to be repaired;
    moving a magazine defining a first chamber and a second chamber relative to the reservoir between a first position in which the first chamber is in communication with the reservoir and a second position in which the second chamber is in communication with the reservoir;
    actuating an actuation member to slide a plunger into at least one of the first chamber or the second chamber to discharge the substance into a delivery tube attached to a housing;
    detaching the delivery tube from the housing and attaching the delivery tube to an injector; and
    injecting the substance from the delivery tube to the tissue to be repaired.

16. The method of claim 15, wherein the tissue comprises a bone.

17. The method of claim 16, wherein the substance comprises bone graft.

18. The method of claim 15, wherein the actuating step comprising pressing a button.

19. The method of claim 15, wherein the actuating step causes the magazine to move from the first position to the second position.

20. The method of claim 19, wherein the moving step comprises rotating the magazine relative to the housing about a longitudinal axis of the magazine.

* * * * *